United States Patent [19]

Fanger et al.

[11] Patent Number: 6,071,517
[45] Date of Patent: *Jun. 6, 2000

[54] BISPECIFIC HETEROANTIBODIES WITH DUAL EFFECTOR FUNCTIONS

[75] Inventors: Michael W. Fanger, Lebanon; Paul M. Guyre, Hanover, both of N.H.; Edward D. Ball, Norwich, Vt.

[73] Assignee: Medarex, Inc., N.J.

[*] Notice: This patent is subject to a terminal disclaimer.

[21] Appl. No.: 08/359,931

[22] Filed: Dec. 20, 1994

Related U.S. Application Data

[63] Continuation of application No. 08/226,388, Apr. 12, 1994, abandoned, which is a continuation of application No. 07/972,871, Nov. 4, 1992, abandoned, which is a continuation of application No. 07/424,540, Oct. 20, 1989, abandoned, which is a continuation-in-part of application No. 07/151,450, Feb. 2, 1988, abandoned, which is a continuation-in-part of application No. 07/069,412, Jul. 1, 1987, Pat. No. 4,954,617, which is a continuation-in-part of application No. 06/882,181, Jul. 7, 1986, abandoned.

[51] Int. Cl.$^7$ .................................................. A61K 39/395
[52] U.S. Cl. ..................... 424/136.1; 424/154.1; 424/155.1; 424/173.1; 424/174.1; 530/387.3; 530/388.2; 530/388.3; 530/388.8; 435/328
[58] Field of Search ................. 424/136.1, 154.1, 424/155.1, 173.1, 174.1, 183.1; 435/70.21, 172.2, 325, 328, 449, 451, 452; 436/548; 530/387.3, 388.1, 388.73, 388.8, 389.6, 389.7, 391.7, 388.2, 388.3

[56] References Cited

U.S. PATENT DOCUMENTS

| | | |
|---|---|---|
| 4,676,980 | 6/1987 | Segal et al. . |
| 4,954,617 | 9/1990 | Fanger et al. ......................... 530/388.8 |

OTHER PUBLICATIONS

Brennan et al., "Preparation of Bispecific Antibodies by Chemical Recombination of Monoclonal Immunoglobulin G$_1$ Fragments," *Science* 229:81–83, Jul. 5, 1985.

Dillman, R.O., "Monoclonal Antibodies for Treating Cancer," *Annals Int. Med* 111:592–602, Oct. 1, 1989.

Hird et al., "Immunotherapy with Monoclonal Antibodies," in *Genes and Cancer*, Carney et al. Eds., Wiley & Sons, 1990.

Clark et al. (1990) in *Bispecific Antibodies and Targeted Cellular Cytotoxicity* (Romet–Lemonne et al., eds.) Fondation Nationale de Transfusion Sanguine, Les Ulis, France pp. 243–247.

de Leij et al. (1990) in *Bispecific Antibodies and Targeted Cellular Cytotoxicity* (Romet–Lemonne et al., eds.) Fondation Nationale de Transfusion Sanguine, Les Ulis, France pp. 249–253.

Nitta et al. (Feb. 17, 1990) *The Lancet* pp. 368–371.

Ball et al. (1992) *J. Hematotherapy* 1:85–94.

Anderson et al., *J. Biol. Chem.* 261:12856 (1986).

Shen et al., *J. Immunol.* 137:3378–3382 (1986).

Karpovsky et al., *J. Exp. Med.* 160:1686–1701 (1984).

Ball et al., *J. Immun.* 130:2937–2941 (1983).

Waldmann, T.A., "Monoclonal Antibodies in Diagnosis and Therapy," *Science* 252:1657–1662, Jun. 21, 1991.

Shen, et al., "Heteroantibody–Mediated Cytotoxicity: Antibody to the High Affinity Fc Receptor for IgG Mediates Cytotoxicity by Human Monocytes That Is Enhanced by Interferon–γ and is not Blocked by Human IgG," *J. Immunol.* 137:3378–3382, 1986.

Karpovsky et al., "Production of Target Specific Effector Cells Using Hetero–Cross–Linked Aggregates Containing Anti–Target Cell and Anti–Fcγ Receptor Antibodies," *J. Exp. Med.* 160:1686–1701, 1984.

Anderson et al., "Monoclonal Antibodies to Fc Receptors for IgG on Human Mononuclear Phagocytes," *J. Biol. Chem.* 261:12856–12864, 1986.

Ball et al., "A Unique Antigen Expressed On Myeloid Cells and Acute Leukemia Blast Cells Defined by a Monoclonal Antibody," *J. Immunol.* 130:2937–2941, 1983.

*Primary Examiner*—Donna Wortman
*Attorney, Agent, or Firm*—Lahive & Cockfield, LLP; Jane E. Remillard; Guilio A. DeConti, Jr.

[57] ABSTRACT

Bispecific molecules which react both with the high-affinity Fcγ receptor of human effector cells and with a target cell surface antigen are disclosed. Binding of the molecules to the Fc receptors found on effector cells is not blocked by human immunoglobulin G. The molecules are useful for targeting human effector cells (e.g. macrophages) against cells bearing the target antigen. For this purpose, bispecific molecules can be constructed containing the binding region derived from an anti-Fcγ receptor antibody and the binding region derived from an antibody specific for the target antigen. Targeted effector cells can be used to destroy cells bearing the target cell surface antigen by cell-mediated antibody dependent cytolysis and by complement-fixation.

44 Claims, No Drawings

BISPECIFIC HETEROANTIBODIES WITH DUAL EFFECTOR FUNCTIONS

RELATED APPLICATIONS

This application is a continuation of U.S. Ser. No. 08/226,388 filed Apr. 12, 1994, now abandoned, which is a continuation of U.S. Ser. No. 07/972,871 filed Nov. 4, 1992, now abandoned, which is a continuation of U.S. Ser. No. 07/424,540 filed Oct. 20, 1989, now abandoned, which is a continuation-in-part of U.S. Ser. No. 07/151,450 filed Feb. 2, 1988, now abandoned, which is a continuation-in-part of U.S. Ser. No. 07/069,412 filed Jul. 1, 1987, now U.S. Pat. No. 4,954,617, which is a continuation-in-part of Ser. No. 06/882,181 filed Jul. 7, 1986, now abandoned.

BACKGROUND

The production of heteroantibodies for targeting effector cells comprising an antibody specific for the high affinity FcRI receptor linked to a second antibody specific for an antigen present on a target cell has been described. See, for example, Segal et al., U.S. Pat. No. 4,676,980; and Karpovsky et al., *J. Exp. Med.* 160:1686–1701 (1984). Such constructs can be used to specifically kill unwanted cells (e.g. tumor cells or virus infected cells).

Recently, a monoclonal antibody has been produced which reacts with the high affinity Fc-gamma receptor through its variable region. Serum immunoglobulin does not compete with the antibody for binding to the Fc receptor. See, for example, Application; Anderson et al., *J. Biol. Chem.* 261:12856 (1986); and Shen et al, *J. Immunol.* 137:3378–3382 (1986). Consequently, serum IgG does not interfere with targeted effector cell killing.

SUMMARY OF THE INVENTION

This invention pertains to bispecific hetero-antibodies comprising an antibody or fragment thereof which can bind a cell surface antigen of a target cell and an antibody which binds the high affinity Fc-γ receptor of an effector cell. The heteroantibodies are capable of inducing complement-mediated and effector-cell-mediated cell lysis. The antibody specific for the Fcγ receptor binds to a site which is distinct from the ligand binding site for the Fc region of IgG and this binding is not blocked by IgG. The bispecific molecules are capable of binding to IgG-occupied receptor of effector cells in the presence of normal serum IgG.

In a preferred embodiment, the antibody specific for the cell surface antigen of the target cell is an IgM molecule. Heteroantibodies formed with IgM can induce complement-mediated, as well as effector-cell-mediated, lysis of the target cell.

The heteroantibodies of this invention can be used to target and destroy unwanted cells such as tumor cells or virus infected cells. For this purpose, they can be administered alone or they can be pre-attached to effector cells for administration to a patient. They can also be used in conjunction with other molecules. For example, molecules of this invention can be used with cytokines such as interferon-γ which can activate or enhance their therapeutic potential.

DETAILED DESCRIPTION OF THE INVENTION

The heteroantibodies of this invention have at least two distinct binding specificities. The molecules contain an antibody or fragment thereof specific for a surface antigen of a target cell and an antibody or fragment thereof specific for the high affinity Fcγ receptor of effector cells. In addition, the heteroantibodies of this invention have dual effector functions. The heteroantibody is capable of inducing complement-mediated cell lysis and antibody-dependent cell mediated cytolysis.

The Fc-receptor binding specificity is provided by a binding agent which binds to the high affinity (p72) Fcγ receptor (FcRI) for human IgG without being blocked by human IgG. The preferred Fcγ receptor binding agent is an antibody, antibody fragment, antibody variable region, or genetic construct having the following characteristics:

a. it reacts specifically with the high affinity Fcγ receptor;

b. it reacts with the receptor through its antigen combining region independent of any Fc portion;

c. it reacts with an epitope of Fcγ receptor which is distinct from the Fc binding (i.e. ligand binding) site of the receptor; and d. it binds ligand-occupied receptor.

The anti-Fcγ receptor antibodies of this invention can be produced as described in U.S. patent application Ser. No. 151,450; Fanger et al., "Monoclonal Antibodies to Fc Receptors for Immunoglobulin G on Human Mononuclear Phagocytes", the teachings of which are incorporated by reference herein. A hybridoma producing a preferred antibody having the above characteristics, mAb 32.2, is available from the American Type Culture Collection, 12301 Parklawn Drive, Rockville, Md. 20852, which was deposited under the provisions of the Budapest Treaty on Jul. 1, 1987. (ATCC accession number HB 9469).

The target cell specificity and the complement-mediated cell lysis effector function is provided by an antibody specific for a surface antigen of the target cell. In a preferred embodiment, this antibody is an antibody which can direct complement-mediated cell lysis and provide the heteroantibody with this effector function. Preferably, the antibody specific for the target cell is an IgM. Heteroantibodies containing antibodies of this class demonstrate enhanced ability to kill targeted cells as is demonstrated in the Example which follows.

Target cells are cells whose elimination would be beneficial to the host. One important type of target cell is a tumor cell. Heteroantibody of this invention can have specificity for FcRI and specificity for a tumor-associated or tumor specific antigen.

Antibodies with a desired tumor specificity for production of heteroantibody can be produced or can be selected from available sources. Monoclonal antibodies against tumor-associated antigens can be made by the methods of Koprowski et al., U.S. Pat. No. 4,172,124. Many suitable anti-tumor antibodies are presently available.

Specific anti-tumor antibodies would include, but not be limited to:

| Antibody | Specificity |
| --- | --- |
| AML-2-23, PM-81, PMN-6, PMN-19 | Myeloid Leukemia |
| SCCL-1, SCCL-175 | Small Cell Lung Carcinoma |
| OC125, OVCT-3 | Ovarian Carcinoma |
| COL-1, COL-2, . . . COL-13 | Colon Carcinoma |

A preferred anti-tumor antibody is an antibody specific for the CD15 antigen as represented by the antibody designated PM-81 in the above table. The CD15 antigen is expressed by colon and breast tumor cells in addition to myeloid leukemia cells (as indicated in the table). A hybridoma producing the PM-81 antibody has been deposited with the American Type Culture Collection and assigned accession number CRL 10266.

In addition to tumor cells, the effector cell can be targeted against auto-antibody producing lymphocytes for treatment of autoimmune disease or an IgE-producing lymphocyte for treatment of allergy. The target can also be a microorganism (bacterium or virus) or a soluble antigen (such as rheumatoid factor or other auto-antibodies).

Bivalent heteroantibodies of this invention comprise an antibody (or fragment) specific for Fcγ receptor, coupled to an antibody (or fragment) specific for a cell surface antigen of a target cell. Heteroantibodies can be prepared by conjugating Fcγ receptor antibody with antibody specific for the target cell antigen as is described in detail in the Example below. A variety of coupling or crosslinking agents can be used to conjugate the antibodies. Examples are protein A, carboiimide, dimaleimide, dithio-bis-nitrobenzoic acid (DTNB), and N-succinimidyl-3-(2-pyridyldithio) propionate (SPDP). SPDP and DTNB are the preferred agents; procedures for crosslinking antibodies with these agents are known in the art. See e.g., Karpovsky, B. et al., (1984) *J. Exp. Med.* 160:1686; Liu, M. A. et al., (1985) *Proc. Natl. Acad. Sci USA* 82:8648; Segal, D. M. and Perez, P., U.S. Pat. No. 4,676,980 (Jun. 30, 1987); and Brennan, M. *Biotechniques* 4:424 (1986).

Heteroantibodies of this invention can be administered to target the killing of unwanted cells in two general ways. The molecules can be given in free form. Alternatively, the molecules can be attached to the surface of effector cells in vitro and the cells can be administered. In each mode the principle is the same; the effector cell is targeted toward the cell bearing the targeted antigen.

Effector cells for targeting are human leukocytes, preferably macrophages. Other cells can include monocytes, activated neutrophils, and possibly activated natural killer (NK) cells and eosinophils. Macrophages can be treated with IFN-γ before targeting to increase the number of Fc receptors for attachment of the targeting antibody or heteroantibody. Neutrophils and NK cells can also be activated with IFN-γ in this way. The effector cells may also be activated before targeting by other cytokines such as tumor necrosis factor, lymphotoxin, colony stimulating factor, and interleukin-2. If desired, effector cells for targeting can be obtained from the host to be treated, or any other immunologically-compatible donor.

The targeted effector cells can be administered as a suspension of cells in a physiologically acceptable solution. The number of cells administered can be in the order of $10^8$–$10^9$, but will vary depending on the therapeutic purpose. In general, the amount will be sufficient to obtain localization of the effector cell at the target cell, and to effect killing of the cell by complement mediated cell lysis and antibody dependent cell-mediated cytolysis (ADCC) and/or phagocytosis. Routes of administration can also vary. The targeted effector cells could be administered intravenously, intramuscularly, or intraperitoneally.

Heteroantibodies of this invention link antigen-specific binding agents to FcγR on effector cells in such a way that the large excess of human IgG in vivo does not interfere with binding of the molecule to effector cells or interfere with functioning of effector cells. This is possible because the anti-FcγR component of these molecules binds to FcγR at an epitope outside of its ligand binding domain. Effector cells (i.e. macrophages) targeted in this way can be employed to bring about antibody-dependent cell-mediated killing of HIV or HIV-infected cells.

The heteroantibodies of this invention have a potentially long half-life in vivo. This can result from the interaction of these constructs with FcγR on all monocytes and macrophages where it might remain for long periods of time, much of it out of circulation, but functionally active throughout the body on all cells of the reticuloendothelial system.

The invention is illustrated further by the following example.

EXAMPLES

Antibodies and Antibody Fragments

The development and properties of mAb 32.2, a mouse mAb to the human monocyte high affinity Fc receptor, have been reported (Anderson, C. L. et al. (1986) *J. Biol. Chem.* 261:12856). Briefly, FcRI was isolated from U937 cells by affinity chromatography on immobilized human IgG and was injected into BALB/c mice. Five days after the last immunization, the splenocytes were fused with cells of the NS1 myeloma cell line. Supernatants of the hybrids were screened for their reactivity with U937 cells by an indirect immunofluorescence assay using a flow cytometer.

Selected hybrids cloned by limiting dilution, were rescreened and expanded. An IgG1 mAb was then selected that exhibited specific binding to the same 72,000 dalton protein (FcRI) precipitated by Sepharose-human IgG. This identity of reaction was shown by preclearing experiments and by identical isoelectric focussing patterns. Binding of mAb 32.2 to FcRI was independent of the Fc region of the antibody inasmuch as Fab' fragments of this mAb affinity adsorbed FcRI. The binding of both mAb 32.2 and human IgG1 to the intact U937 cell were not reciprocally inhibitory, indicating that mAb 32.2 does not interfere with the ligand binding site of FcRI. The IgG fraction of ascites fluid from pristane-primed mice injected with the 32.2 hybridoma was obtained by precipitation with 40% saturated ammonium sulfate. Ion exchange high pressure liquid chromatography (HPLC) with the use of a protein-pak 5PW DEAE column (Waters Chromatography Division, Millipore, Milford, Mass.) was used to purify the 32.2 IgG1 antibody. The F(ab')$_2$ fragment was made according to the method of Parham (Parham, P. (1983) *J. Immunol.* 131:2895) by pepsin digestion at pH 3.5. Digestions were monitored by HPLC to ensure complete cleavage. F(ab')$_2$ fragments were purified by HPLC gel filtration chromatography by using a Bio-Sil TSK 250 column (Bio-Rad, Richmond, Calif.), and Fab fragments were obtained by reduction with 1 mM dithiothreitol for 2 hr at 18° C., followed by alkylation with 2 mM iodoacetamide for 1 hr at 18° C.

A hybridoma producing an IgM mAb, PM81, which reacts specifically with the CD15 cell surface antigen has been deposited with the American Type Culture Collection CRL 10266.

Heteroantibody Formation

Heteroantibodies of Fab 32.2 plus mAb PM81 were made by the method of Karpovsky et al. (Karpovsky, B. (1984) *J. Exp. Med.* 160:1686). Fab 32.2 (or Fab W6/32) and mAb PM81 (at 1 to 3 mg/ml) were treated separately with an eightfold molar excess of the bifunctional reagent N-succinimidyl-3-(2 pyridyl-dithiol) propionate (SPDP) (Pharmacia, Uppsala, Sweden) for 2 hr at 18° C. SPDP-treated Fab 32.2 was dialyzed in phosphate-buffered saline (PBS), pH 7.4. SPDP-treated mAb PM81 was dialyzed in 0.1 M phosphate-0.1 M acetate-0.1 M NaCl, pH 4.5, was treated with 0.02 M dithiothreitol (30 min. 18° C.), and was passed through a G-25 Sephadex column (Pharmacia) equilibrated in 0.1 M phosphate, 0.1 M NaCl, pH 7.5. Equimolar amounts of the Fab 32.2 and mAb PM81 were then mixed and incubated at 18° C. for 4 hr, after which cross-linking was terminated with 1 mM iodoacetamide. Heteroantibodies were dialyzed into PBS and were sterilized by 0.2 μm filtration. Preparations contained less than 15% uncross-linked Fab, and were at a concentration of 0.7 to 1.5 $OD_{280}$ U per ml.

Effector Cells

U937 cells obtained from the ATCC (Sundstrom C., and K. Nilsson (1976) *Int. J. Cancer* 17:565) were cultured in RPMI containing 10% heat-inactivated fetal bovine serum (FBS) and gentamicin (RPMI-FBS). Monocytes were purified from cytophoresis packs obtained from normal volunteers, as described (Shen, L. et al. (1986) *Clin. Exp. Immunol.* 65:387). Briefly, cells from cytophoresis packs were spun on Ficoll-Hypaque and the interface layer was collected. After three washes in RPMI, the cells were resuspended in RPMI-FBS at $5\times10^7$/ml in 15 ml polypropylene tubes and were rotated at 8 rpm for 1 hr at 4° C. to induce monocyte clumping. The clumped cells were sedimented on ice at 1×G for 15 to 30 min, the supernatant was removed, and the cells (in 2 ml of medium) were then carefully layered onto an equal volume of ice-cold FBS. After sedimentation through the FBS for 20 min at 4° C., the lower phase contained 60 to 95% monocytes, the remainder being lymphocytes. Monocytes were washed twice in RPMI-FBS, were brought to $2\times10^6$/ml in RPMI-FBS, and then were assayed. In some experiments, U937 cells ($5\times10^5$/ml or monocytes ($2\times10^6$/ml) were cultured for 18 to 24 hr in RPMI-FBS supplemented with 300 international reference units (IRU)/ml of recombinant human interferon-γ (Genetech, San Francisco, Calif.).

Target-Cells

HL-60 leukemia cells (ATCC CCL 240) were labeled for 1 hr at 37° C. with 200 μCi of $^{51}$Cr sodium chromate in normal saline (New England Nuclear, Boston, Mass.). Cells were washed three times in medium 199–10% FBS before use.

Antibody-Dependent Cellular Cytotoxicity (ADCC)

Equal volumes (50 μl) of $^{51}$Cr-labeled target cells at $5\times10^5$/ml, effector cells at various effector to target ratios, and heteroantibodies at the concentrations indicated were mixed in round-bottomed microtiter wells. All tests were conducted in triplicate. Controls for the effects of heteroantibodies alone, and effector cells alone, were included in all experiments. Maximal lysis was obtained by the addition of 100 μl of 2% sodium dodecyl sulfate in water to 50 μl of CE. Plates were incubated for 18 hr at 37° C., after which 50% of the supernatant was removed and then counted for release of $^{51}$Cr. Percent cytotoxicity was calculated at 100×(counts released with effectors+antibody)−(counts released with effectors alone)÷(maximum lysis−spontaneous release). The results were expressed as mean±standard deviation of triplicates.

Cellular Heteroconjuguates

Target cells were coated for 2 hr at 4° C. with heteroantibodies at the concentrations indicated, were washed three times, and were adjusted to $2\times10^7$ cells/ml. Equal volumes (50 μl) of targets and effectors ($2\times10^6$/ml) were mixed by gentle rotation for 1 hr at 4° C., and then allowed to settle for 1 hr on ice. The supernatant was removed and the cells were gently resuspended in 100 μl of acridine orange and examined in a hemocytometer by using incident light and UV. Effector cells (200) in duplicate samples were scored for attachment to one or more CE target cells.

Microtiter Binding Assay

A monolayer of target cells was incubated in a microtitre plate well at 4° C. with the heteroantibody construct. Unbound heteroantibodies were removed in a wash step. MTT labelled effector cells were added. MTT was then dissolved in isopropanol and a reading was taken using an ELISA reader at A 570.

Results

The ability of the bispecific heteroantibody to mediate attachment of human monocytes to tumor target cells was confirmed in a microtiter well assay using MTT labelled monocytes and THP-1 human monocytic leukemia (ATCC TIB 202) or SKBR-3 breast carcinoma (ATCC HTB 30) target cells.

The ability of the heteroantibody to mediate killing of HL-60 promyelocytic leukemia cells was studied in the ADCC assay. Monocytes alone caused minimal killing (5–20%), monocytes plus bispecific heteroantibody caused moderate killing (20–50%), and monocytes plus bispecific heteroantibody plus human serum resulted in maximal killing (50–80%).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A heteroantibody comprising a first antibody or fragment thereof which binds to a cell surface antigen and a second antibody or fragment thereof which binds to the high affinity Fc-γ receptor of an effector cell without being blocked by human immunoglobulin G, wherein said heteroantibody is capable of inducing complement mediated and effector-cell-mediated cell lysis.

2. The heteroantibody of claim 1, wherein the first antibody or fragment thereof comprises an IgM molecule.

3. The heteroantibody of claim 1, wherein the first antibody or fragment thereof binds to a CD15 cell surface antigen and the second antibody or fragment thereof binds to the high affinity Fc-γ receptor of an effector cell.

4. The heteroantibody of claim 3, wherein the first antibody or fragment thereof comprises an IgM molecule.

5. The heteroantibody of claim 3, wherein the first antibody or fragment thereof and the second antibody or fragment thereof are linked by a disulfide bridge.

6. The heteroantibody of claim 3, wherein the second antibody or fragment thereof is a monoclonal antibody which is produced by the hybridoma having ATCC accession number HB 9469.

7. The heteroantibody of claim 3, wherein the second antibody fragment is an FAb fragment of the monoclonal antibody produced by the hybridoma having ATCC accession number HB 9469.

8. The heteroantibody of claim 3, wherein the effector cell is a human cell selected from the group consisting of monocytes, macrophages, neutrophils and eosinophils.

9. The heteroantibody of claim 3, wherein the CD15 cell surface antigen is present in a tumor cell which is selected from the group consisting of myeloid leukemia, lung small cell carcinoma, colon carcinoma and breast carcinoma.

10. The heteroantibody of claim 1, wherein the first antibody or fragment thereof comprises mAb PM81 which is produced by the hybridoma having ATCC accession number CRL 10266, and the second antibody or fragment thereof comprises mAb 32.2 which is produced by the hybridoma having ATCC accession number HB 9469.

11. A heteroantibody of claim 1, wherein the cell surface antigen is a breast carcinoma antigen.

12. A target-specific effector cell comprising:
   a) an effector cell expressing high affinity receptor for the Fc portion of IgG; and
   b) the heteroantibody of claim 11.

13. A method of tumor therapy comprising, administering to a patient afflicted with a tumor, a therapeutic amount of the target-specific effector cells of claim 12.

14. A heteroantibody of claim 1, wherein the cell surface antigen is an ovarian carcinoma antigen.

15. A target-specific effector cell comprising:
  a) an effector cell expressing high affinity receptor for the Fc portion of IgG; and
  b) the heteroantibody of claim 14.

16. A method of tumor therapy comprising, administering to a patient afflicted with a tumor, a therapeutic amount of the target-specific effector cells of claim 15.

17. A target-specific effector cell comprising:
  a) an effector cell expressing high affinity receptor for the Fc portion of IgG; and
  b) a heteroantibody which is bound to an epitope of the Fc receptor of the effector cell that is outside of the ligand binding domain of the receptor, and is capable of inducing complement-mediated and effector cell-mediated cell lysis, said heteroantibody comprising:
    (i) a first antibody or fragment thereof which binds to a CD15 cell surface antigen; and
    (ii) a second antibody or fragment thereof which binds to an effector cell high affinity Fcγ receptor without being blocked by human immunoglobulin G.

18. A target-specific cell of claim 17, wherein the first antibody or fragment thereof comprises an IgM.

19. A target-specific effector cell of claim 17, wherein the first antibody or fragment thereof and the second antibody or fragment thereof are linked by a disulfide bridge.

20. A target-specific effector cell of claim 17, wherein the second antibody or fragment thereof is produced by the hybridoma having ATCC accession number HB 9469.

21. A target specific effector cell of claim 17, wherein the antibody fragment which binds to the high affinity Fc-γ receptor is an FAb fragment of the monoclonal antibody produced by the hybridoma having ATCC accession number HB 9469.

22. A target-specific effector cell of claim 17, wherein the effector cell is a human cell selected from the group consisting of monocytes, macrophages, neutrophils and eosinophils.

23. A target specific effector cell of claim 17, wherein the tumor cell is selected from the group consisting of myeloid leukemia, lung small cell carcinoma, colon carcinoma and breast carcinoma.

24. A target-specific effector cell comprising:
  a) an effector cell expressing high affinity Fc-γ receptor;
  b) a heteroantibody which is bound to an epitope of the Fc receptor of the effector cell that is outside the binding domain of the receptor, and is capable of inducing complement-mediated and effector cell-mediated cell lysis, said heteroantibody comprising:
    (i) mAb PM81 which is produced by the hybridoma having ATCC accession number CRL 10266; and
    (ii) mAb 32.2 which is produced by the hybridoma having ATCC accession number HB 9469.

25. A method of tumor therapy, comprising administering to a patient afflicted with a tumor, a therapeutic amount of a targeted effector cell comprising:
  (i) an antibody or fragment thereof which binds to a CD15 cell surface antigen; and
  (ii) an antibody or fragment thereof which binds to a high affinity Fc-γ receptor on an effector cell without being blocked by human immunoglobulin G.

26. The method of claim 25, wherein the antibody which binds to CD15 comprises an IgM.

27. The method of claim 25, wherein the antibody or fragment thereof which binds to CD15 and the antibody or fragment thereof which binds to the high affinity Fc-γ receptor are linked by a disulfide bridge.

28. The method of claim 25, wherein the antibody or fragment thereof which binds to the high affinity Fc-γ receptor is produced by the hybridoma having ATCC accession number HB 9469.

29. The method of claim 25, wherein the antibody fragment which binds to the high affinity Fc-γ receptor is an FAb fragment of the IgG molecule produced by the hybridoma having ATCC accession number HB 9469.

30. The method of claim 25, wherein the effector cell is a human cell selected from the group consisting of monocytes, macrophages, neutrophils and eosinophils.

31. The method of claim 25, wherein the tumor cell is selected from the group consisting of myeloid leukemia, lung small cell carcinoma, colon carcinoma and breast carcinoma.

32. A method of tumor therapy comprising, administering to a patient afflicted with a tumor, a therapeutic amount of a target-specific effector cell comprising:
  a) an effector cell expressing a high affinity Fc-γ receptor;
  b) a heteroantibody which is bound to an epitope of the Fc receptor of the effector cell that is outside the binding domain of the receptor, and is capable of inducing complement-mediated and effector cell-mediated cell lysis, said heteroantibody comprising:
    (i) mAb PM81 which is produced by the hybridoma having ATCC accession number CRL 10266; and
    (ii) mAb 32.2 which is produced by the hybridoma having ATCC accession number HB 9469.

33. A method of inducing cell lysis comprising contacting a target cell with a heteroantibody comprising:
  a first antigen binding region which binds to an Fc receptor for IgG without being blocked by IgG; and
  a second antigen binding region which binds to a target epitope.

34. The method of claim 33, wherein the first antigen binding region is derived from a monoclonal antibody produced by the hybridoma cell line having ATCC accession number HB 9469.

35. The method of claim 33, wherein the second antigen binding region binds to a CD15 cell surface antigen.

36. The method of claim 33, wherein the second antigen binding region is derived from a monoclonal antibody produced by the hybridoma cell line having ATCC accession number CRL 10266.

37. The method of claim 33, wherein the target cell is selected from the group consisting of a tumor cell, an auto-antibody producing cell and an IgE-producing cell.

38. The method of claim 33, wherein the target cell is a tumor cell.

39. The method of claim 38, wherein the tumor cell is selected from the group of tumors consisting of myeloid leukemia, lung small cell carcinoma, colon carcinoma and breast carcinoma.

40. The method of claim 33, wherein the Fc receptor is a high affinity Fcγ receptor.

41. A method of directing an effector cell to a target cell, comprising contacting the effector cell with a heteroantibody comprising:
  an antigen binding region which binds to a high affinity Fc receptor for
  IgG without being blocked by human IgG; and
  an antigen binding region which binds to a target cell.

42. The method of claim 41, wherein the target cell is selected from the group consisting of a tumor cell, an auto-antibody producing cell and an IgE-producing cell.

43. The method of claim 41, wherein the target cell is a tumor cell.

44. The method of claim 41, wherein the effector cell is selected from the group consisting of leukocytes, monocytes, neutrophils, natural killer cells and eosinophils.

* * * * *